(12) United States Patent
Miyake et al.

(10) Patent No.: US 11,384,041 B2
(45) Date of Patent: Jul. 12, 2022

(54) PROCESS FOR PREPARING AN ALKOXYMETHYL ALKYNYL ETHER COMPOUND HAVING A TERMINAL TRIPLE BOND

(71) Applicant: Shin-Etsu Chemical Co., Ltd., Tokyo (JP)

(72) Inventors: Yuki Miyake, Niigata (JP); Miyoshi Yamashita, Niigata (JP); Takeshi Kinsho, Niigata (JP); Akihiro Baba, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 17/128,306

(22) Filed: Dec. 21, 2020

(65) Prior Publication Data

US 2021/0198172 A1 Jul. 1, 2021

(30) Foreign Application Priority Data

Dec. 25, 2019 (JP) .............................. JP2019-235058

(51) Int. Cl.
*C07C 41/52* (2006.01)
*C07C 41/22* (2006.01)

(52) U.S. Cl.
CPC .............. *C07C 41/52* (2013.01); *C07C 41/22* (2013.01)

(58) Field of Classification Search
CPC ................................ C07C 41/52; C07C 41/22
See application file for complete search history.

(56) References Cited

PUBLICATIONS

Berliner et al. ("Synthesis of Alpha-Halo Ethers From Symmetric Acetals and in situ Methoxymethylation of an alcohol", Organic Syntheses, 2007, vol. 84, pp. 102-110). (Year: 2007).*

Lewis, Sr. ("recycling", Hawley's Condensed Chemical Dictionary, twelfth edition, 1993, p. 995). (Year: 1993).*
Extended European Search Report corresponding to European Patent Application No. 20216256.6 (6 pages) (dated May 11, 2021).
Martin et al. "Applications of the Intramolecular Diels-Alder Reactions of Heterodienes to the Synthesis of Indole Alkaloids" Tatrahedron, 42(11):2903-2910 (1986).
Miyakoshi et al. "1,2,3-Triazole-Containing Uracil Derivatives with Excellent Pharmacokinetics as a Novel Class of Potent Human Deoxyuridine Triphosphatase Inhibitors" Journal of Medicinal Chemistry, 55:6427-6437 (2012).
Vrancken et al. "Addition of Hetero Allenyl Copper Reagents to Aldehydes: Scope and Behavior" The Journal of Organic Chemistry, 72:1770-1779 (2007).

* cited by examiner

*Primary Examiner* — Rosalynd A Keys
(74) *Attorney, Agent, or Firm* — Myers Bigel, P.A.

(57) ABSTRACT

The present invention provides a process for preparing an alkoxymethyl alkynyl ether compound having a terminal triple bond of the following formula (4): $H-C\equiv C(CH_2)_a OCH_2OCH_2R$ (4), wherein R represents a hydrogen atom, an n-alkyl group having 1 to 9 carbon atoms, or a phenyl group, and "a" represents an integer of 1 to 10, the method comprising subjecting an alkynol compound having a terminal triple bond of the following formula (1): $H-C\equiv C(CH_2)_aOH$ (1), wherein "a" is as defined above, to an alkoxymethylation with a halomethyl alkyl ether compound of the following formula (3): $RCH_2OCH_2X$ (3), wherein X represents a halogen atom, and R is as defined above, in the presence of a dialkylaniline compound of the following formula (2): $[CH_3(CH_2)_b][CH_3(CH_2)_c]NC_6H_5$ (2), wherein b and c represent, independently of each other, an integer of 0 to 9, to form the alkoxymethyl alkynyl ether compound (4) having a terminal triple bond.

27 Claims, No Drawings

PROCESS FOR PREPARING AN ALKOXYMETHYL ALKYNYL ETHER COMPOUND HAVING A TERMINAL TRIPLE BOND

CROSS-REFERENCE TO RELATED APPLICATION

This U.S. nonprovisional application claims priority to Japanese Application No. 2019-235058 filed Dec. 25, 2019, the entire contents of which are incorporated herein by reference.

TECHNICAL FIELD

The present invention relates to a process for preparing an alkoxymethyl alkynyl ether compound having a terminal triple bond.

BACKGROUND ART

It is conventional first to protect a hydroxyl group of a starting compound with a protecting group, to have another reactive group of the starting compound reacted so as to construct a desired skeleton, and subsequently to remove the protected group in an organic synthesis scheme. A protecting group for a hydroxyl group includes a trimethylsilyl group, an acetyl group, a benzyl group, a benzoyl group, and an alkoxymethyl group such as a methoxymethyl group (MOM group). In particular, an alkoxymethyl group can be used both in acidic and basic reaction conditions and can be easily disconnected for deprotection in acid hydrolysis conditions. Accordingly, an alkoxymethyl group is widely used in organic synthesis.

Protecting a hydroxyl group in an alkynol compound having a terminal triple bond using a methoxymethyl group, known as alkoxymethylation, is reported in the following Non-Patent Literature 1, wherein chloromethyl methyl ether is added dropwise to an alkynol compound in the presence of a base in a solvent and in the following Non-Patent Literature 2, wherein an alkynol compound is reacted with dimethoxymethane in the presence of an acid catalyst and lithium halide.

LIST OF THE PRIOR ART

[Non-Patent Literature 1] Masayoshi Fukuoka et al., J. Med. Chem., 2012, 55, 6427-6437.
[Non-Patent Literature 2] Emmanuel Vrancken et al., J. Org. Chem. 2007, 72, 1770-1779.

SUMMARY OF THE INVENTION

In Non-Patent Literature 1, dichloromethane is used as a solvent, which is extremely high environmental hazard. The base, N,N-diisopropylethylamine, is used in a large amount and all transferred into a waste water in the post-treatment after the reaction. Therefore, this method is unfavorable in view of environmental protection and economy. Recovery and purification of the base from the waste water is complicated and costly with low recovery efficiency. Incineration of the whole waste water requires vast costs and is thus unfavorable in terms of economy and is, in addition, undesirable for environmental protection. After the reactions, diethyl ether is used as an extraction solvent to extract 4-(methoxymethoxy)-1-butyne, which is water soluble, into an organic phase. Diethyl ether has a low boiling point and is flammable. The process has a yield as extremely low as 58%. These make this method industrially disadvantageous.

In Non-Patent Literature 2, use is made of an expensive lithium halide, which makes the method uneconomical. A large excessive amount of dimethoxymethane is required to shift the equilibrium to complete the reaction. This decreases productivity of the method, and a yield is as low as 75%. After the reactions, diethyl ether is used as an extraction solvent to extract 3-(methoxymethoxy)-1-propylene, which is water soluble, into an organic phase. Diethyl ether has a low boiling point and is flammable. This makes the method industrially disadvantageous. Because the reaction is an equilibrium reaction, the product, an alkoxymethyl alkynyl ether compound, contains a starting material, an alkynol compound. In particular, in a case of alkoxymethylation of a lower alkynol compound having a lower molecular weight, a starting alkynol compound and a product alkoxymethyl alkynyl ether compound may have a small difference in boiling points, which makes separation by distillation difficult.

In a case of a lower alkynol compound having 3 to 6 carbon atoms, a methoxymethyl alkynyl ether compound protected with a methoxymethyl group is soluble in water. When an extraction solvent is not used, loss of the product into an aqueous phase is larger, leading to a largely lowered yield. Alkoxymethyl alkynyl ether compounds of such a lower alkynol compound have low boiling points which are close to those of solvents such as toluene and xylene. This makes separation by distillation difficult. Use of a solvent may reduce the amounts of raw materials to be fed into a reaction vessel, resulting in decreased productivity.

The present invention aims to overcome the aforesaid problems and to prepare an alkoxymethyl alkynyl ether compound having a terminal triple bond from an alkynol compound having a terminal triple bond in a high yield. The present invention aims also to provide an environmentally preferred and economical process for preparing an alkoxymethyl alkynyl ether compound.

As a result of the intensive researches, the present inventors have found that an alkoxymethyl alkynyl ether compound having a terminal triple bond may be prepared in a high yield by a way of protecting a hydroxyl group of an alkynol compound having a terminal triple bond with an alkoxymethyl group and using a dialkylaniline compound as a base and extraction solvent. The present inventors have also found that the dialkylaniline compound used as a base and extraction solvent may be recovered in a high yield, and reused in a subsequent alkoxymethylation. Thus, the present invention has been invented.

An embodiment of the present invention provides a process for preparing an alkoxymethyl alkynyl ether compound having a terminal triple bond of the following formula (4):

$$H—C≡C(CH_2)_aOCH_2OCH_2R \quad (4)$$

wherein R represents a hydrogen atom, an n-alkyl group having 1 to 9 carbon atoms, or a phenyl group, and "a" represents an integer of 1 to 10, the method comprising subjecting an alkynol compound having a terminal triple bond of the following formula (1):

$$H—C≡C(CH_2)_aOH \quad (1)$$

wherein a is as defined above,
to an alkoxymethylation with a halomethyl alkyl ether compound of the following formula (3):

$$RCH_2OCH_2X \quad (3)$$

wherein X represents a halogen atom, and R is as defined above, in the presence of a dialkylaniline compound of the following formula (2):

$$[CH_3(CH_2)_b][CH_3(CH_2)_c]NC_6H_5 \quad (2)$$

wherein b and c represent, independently of each other, an integer of 0 to 9, to form the alkoxymethyl alkynyl ether compound (4) having a terminal triple bond.

In another embodiment of the present invention, the process comprises a step of recovering the dialkylaniline compound (2) after the alkoxymethylation. Another embodiment of the invention comprises reuse of the recovered dialkylaniline compound (2) in a subsequent alkoxymethylation.

According to the present invention, the base used in an alkoxymethylation, namely the dialkylaniline compound (2), may work also as an extraction solvent. Therefore, any solvent in the alkoxymethylation or in extraction after the reaction is unnecessary. According to the present invention, the alkoxymethyl alkynyl ether compound (4) may be prepared with less costs in high productivity, high purity and high yield. The dialkylaniline compound (2) used in the reaction may be recovered in a high yield, and reused in a subsequent alkoxymethylation.

Specifically, owing to the use of the dialkylaniline compound (2) is as a base and extraction solvent in the present invention, a hydroxyl group of the alkynol compound having a terminal triple bond is alkoxymethylated with excellent reactivity even without any additional solvent. After the alkoxymethylation, the dialkylaniline compound (2) serves as an extraction solvent, which make it possible to recover the alkoxymethyl alkynyl ether compound (4) having a terminal triple bond in a high yield without any additional extraction solvent. In the present invention in which the dialkylaniline compound (2) is used as a base and extraction solvent, the dialkylaniline compound (2) may be separated from the alkoxymethyl alkynyl ether compound (4) by distillation and recovered in high purity and a high yield, and the recovered dialkylaniline compound (2) may be reused in a subsequent alkoxymethylation.

DETAILED DESCRIPTION OF THE PREFERRED EMBODIMENTS

The alkoxymethylation of the present invention is carried out by reacting an alkynol compound having a terminal triple bond of the following formula (1) (hereinafter referred to also as "alkynol compound (1)") with a halomethyl alkyl ether compound of the following formula (3) (hereinafter referred to also as "halomethyl alkyl ether compound (3)") in the presence of a dialkylaniline compound of the following formula (2) (hereinafter referred to also as "dialkylaniline compound (2)") to form an alkoxymethyl alkynyl ether compound having a terminal triple bond of the following formula (4) (hereinafter referred to also as "alkoxymethyl alkynyl ether compound (4)").

$$H-C\equiv C(CH_2)_aOH \quad (1)$$

$$[CH_3(CH_2)_b][CH_3(CH_2)_c]NC_6H_5 \quad (2)$$

$$RCH_2OCH_2X \quad (3)$$

$$H-C\equiv C(CH_2)_aOCH_2OCH_2R \quad (4)$$

First, the alkynol compound (1) will be described hereinafter.

In the formula (1), "a" represents an integer of 1 to 10, preferably 1 to 4.

Specific examples of the alkynol compound (1) include 2-propyn-1-ol, 3-butyn-1-ol, 4-pentyn-1-ol, 5-hexyn-1-ol, 6-heptyn-1-ol, 7-octyn-1-ol, 8-nonyn-1-ol, 9-decyn-1-ol, 10-undecyn-1-ol, and 11-dodecyn-1-ol.

Of the alkynol compound (1), lower alkynol compounds which comprise a terminal triple bond and 3 to 6 carbon atoms (i.e., a=1 to 4) and is highly water solubility, namely 2-propyn-1-ol, 3-butyn-1-ol, 4-pentyn-1-ol, and 5-hexyn-1-ol, are particularly advantageous in the preparation of the alkoxymethyl alkynyl ether compound (4) which is of a form of being protected with the lower alkynol compound. When an alkoxymethyl alkynyl ether compound is prepared by alkoxymethylating such a lower alkynol compound having a terminal triple bonds, dichloromethane or diethyl ether, which is insoluble in water and has a high extraction ability and a low boiling point, is usually required as a solvent in the reaction or as an extraction solvent. Then, the solvent occupies a space of a reaction vessel to decrease amounts of the raw materials to be fed into the reaction vessel and worsen productivity. The solvent must be later separated by distillation and will be discarded to causes environmental pollution. Meanwhile, if such a solvent is not used, a part of the alkoxymethyl alkynyl ether compound (4) remains in an aqueous phase, resulting in an extremely lowered yield of the alkoxymethyl alkynyl ether compound (4). However, in the present invention, the high extraction ability of the dialkylaniline compound (2) allows extraction of the alkoxymethyl alkynyl ether compound (4), which is a protected form of the lower alkynol compound, into the organic phase without being transferred into the aqueous phase. Accordingly, productivity of the alkoxymethyl alkynyl ether compound (4) is increased by utilizing the dialkylaniline compound (2) as a base in the alkoxymethylation and as an extraction solvent after the alkoxymethylation.

The alkynol compound (1) may be commercially available one or may be prepared in house.

Next, the dialkylaniline compound (2) will be described hereinafter.

In the formula (2), b and c represent, independently of each other, an integer of 0 to 9, preferably 0 to 3.

The dialkylaniline compound (2) works as a base and an extraction solvent in the alkoxymethylation.

Water-soluble compounds such as triethylamine can be used as a base in the alkoxymethylation, but not as an extraction solvent after the reaction. Meanwhile, insoluble compounds such as N,N-diisopropylethylamine may work as a base in the alkoxymethylation and further also as an extraction solvent after the reaction. However, such has a low boiling point which is only little different form a boiling point of a product obtained in the alkoxymethylation, particularly, of a lower alkynol compound having 3 to 6 carbon atoms. Then, it is impossible to separate the both and purify the product by distillation.

From these viewpoints, a compound is desirable, which has an ability to act as a base, and an extraction ability, and has a boiling point sufficiently different from that of the product. The dialkylaniline compound is selected so as to secure a boiling point sufficiently different from that of the alkoxymethyl alkynyl ether compound (4). Then, the two compounds are easily separated by distillation and the recovered dialkylaniline compound may be reused in a subsequent alkoxymethylation, which offers economic benefit. For these reasons, the dialkylaniline compound (2) is adopted in the alkoxymethylation in the present invention.

Specific examples of the dialkylaniline compound (2) include N,N-dimethylaniline, N,N-diethylaniline, N,N-dipropylaniline, N,N-dibutylaniline, N,N-dipentylaniline, N,N-dihexylaniline, N,N-diheptylaniline, N,N-dioctylaniline, N,N-dinonylaniline, N,N-didecylaniline, N,N-ethylmethylaniline, N,N-methylpropylaniline, N,N-butylmethylaniline, N,N-ethylpropylaniline, and N,N-butylethylaniline. In view of the reactivity, N,N-dimethylaniline, N,N-diethylaniline, N,N-dipropylaniline, and N,N-dibutylaniline are preferred, and N,N-diethylaniline is more preferred.

An amount of the dialkylaniline compound (2) used is preferably from 1.0 to 5.0 mol, more preferably from 1.0 to 2.0 mol, per mol of the alkynol compound (1) in view of the productivity.

The dialkylaniline compound (2) may be commercially available one or may be prepared in house.

Next, the halomethyl alkyl ether compound (3) will be described hereinafter.

X in the formula (3) represents a halogen atom, such as a chlorine atom, a bromine atom, and an iodine atom. A chlorine atom is preferred in view of the versatility.

R in the formula (3) represents a hydrogen atom, an n-alkyl group having 1 to 9, preferably 1 to 4 carbon atoms, or a phenyl group.

Specific examples of the n-alkyl group having 1 to 9 carbon atoms include linear alkyl groups such as a methyl group, an ethyl group, an n-propyl group, an n-butyl group, an n-pentyl group, an n-hexyl group, an n-heptyl group, an n-octyl group, and an n-nonyl group.

Specific examples of the halomethyl alkyl ether compound (3) include chloromethyl methyl ether, chloromethyl ethyl ether, chloromethyl propyl ether, chloromethyl butyl ether, chloromethyl pentyl ether, chloromethyl hexyl ether, chloromethyl heptyl ether, chloromethyl octyl ether, chloromethyl nonyl ether, chloromethyl decyl ether, chloromethyl benzyl ether, bromomethyl methyl ether, bromomethyl ethyl ether, bromomethyl propyl ether, bromomethyl butyl ether, bromomethyl pentyl ether, bromomethyl hexyl ether, bromomethyl heptyl ether, bromomethyl octyl ether, bromomethyl nonyl ether, bromomethyl decyl ether, bromomethyl benzyl ether, iodomethyl methyl ether, iodomethyl ethyl ether, iodomethyl propyl ether, iodomethyl butyl ether, iodomethyl pentyl ether, iodomethyl hexyl ether, iodomethyl heptyl ether, iodomethyl octyl ether, iodomethyl nonyl ether, iodomethyl decyl ether, and iodomethyl benzyl ether. In view of the versatility, chloromethyl methyl ether, chloromethyl ethyl ether, chloromethyl propyl ether, chloromethyl butyl ether, and chloromethyl benzyl ether are preferred, and chloromethyl methyl ether and chloromethyl ethyl ether are more preferred.

An amount of the halomethyl alkyl ether compound (3) used is preferably from 1.0 to 3.0 mol, more preferably from 1.0 to 1.8 mol, per mol of the alkynol compound (1) in view of the reactivity.

The halomethyl alkyl ether compound (3) may be commercially available one or may be prepared in house.

For instance, the halomethyl alkyl ether compound (3) is prepared by reacting a dialkoxymethane compound of the following formula (5) (hereinafter referred to as "dialkoxymethane compound (5)") with a halogenating agent (7) in the presence of a zinc compound (6).

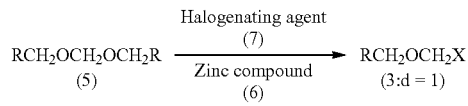

R in the dialkoxymethane compound (5) is the same as R defined for the halomethyl alkyl ether compound (3).

Specific examples of the dialkoxymethane compound (5) include dimethoxymethane, diethoxymethane, dipropoxymethane, dibutoxymethane, dipentyloxymethane, dihexyloxymethane, diheptyloxymethane, dioctyloxymethane, dinonyloxymethane, didecyloxymethane, and dibenzyloxymethane. In view of the versatility, dimethoxymethane, diethoxymethane, dipropoxymethane, dibutoxymethane, and dibenzyloxymethane are preferred, and dimethoxymethane and diethoxymethane are more preferred.

An amount of the dialkoxymethane compound (5) used in the preparation of the halomethyl alkyl ether compound (3) is preferably from 1.0 to 10.0 mol, more preferably from 1.0 to 3.0 mol, per mol, of the alkynol compound (1) in view of the reactivity.

Specific examples of the zinc compound (6) include zinc halides such as zinc chloride, zinc bromide, and zinc iodide; acetate salts such as zinc acetate; and trifluoromethanesulfonate salts such as zinc trifluoromethanesulfonate. Zinc halides are preferred in view of the versatility.

An amount of the zinc compound (6) used in the preparation of the halomethyl alkyl ether compound (3) is preferably 0.0001 to 5.0 mol, more preferably 0.001 to 1.0 mol, per mol of the alkynol compound (1) in view of the reactivity.

Specific examples of the halogenating agent (7) include oxalyl halide compounds such as oxalyl chloride, oxalyl bromide, and oxalyl iodide; thionyl halide compounds such as thionyl chloride, thionyl bromide, and thionyl iodide; and acid halides such as acetyl chloride, acetyl bromide, acetyl iodide, propionyl chloride, propionyl bromide, propionyl iodide, butyryl chloride, butyryl bromide, butyryl iodide, valeryl chloride, valeryl bromide, valeryl iodide, hexanoyl chloride, hexanoyl bromide, hexanoyl iodide, heptanoyl chloride, heptanoyl bromide, heptanoyl iodide, octanoyl chloride, octanoyl bromide, octanoyl iodide, nonanoyl chloride, nonanoyl bromide, nonanoyl iodide, decanoyl chloride, decanoyl bromide, and decanoyl iodide. Acid halides are preferred in view of the reactivity.

An amount of the halogenating agent (7) used in the preparation of the halomethyl alkyl ether compound (3) is preferably from 1.0 to 10.0 mol, more preferably from 1.0 to 2.8 mol, per mol of the alkynol compound (1) in view of the reactivity.

A reaction temperature in the preparation of the halomethyl alkyl ether compound (3) varies, depending on a boiling point of the dialkoxymethane compound (5) to be used, and is preferably from −40 to 280° C., more preferably from 0 to 80° C., in view of the reactivity.

A reaction time in the preparation of the halomethyl alkyl ether compound (3) varies, depending on a reaction scale, and is preferably from 1 to for 50 hours in view of the productivity.

In the alkoxymethylation, the alkynol compound (1) and the dialkylaniline compound (2) are added dropwise to the halomethyl alkyl ether compound (3) contained in a reactor. The alkynol compound (1) and dialkylaniline compound (2) may be added dropwise separately in this order or in a reverse order or may be added dropwise simultaneously, separately or as a mixture thereof. It is preferred to add a mixture hereof in view of the reactivity.

In the alkoxymethylation, a solvent may be used, if necessary, in addition to the dialkylaniline compound (2) which works also as a base (see, for example, Examples 2 and 3 below).

Examples of the solvent may be usual solvents, for example, ethers such as diethyl ether, dibutyl ether, tetrahydrofuran (THF), 4-methyltetrahydropyran, cyclopentylmethyl ether, and 1,4-dioxane; hydrocarbons such as hexane, heptane, benzene, toluene, xylene, and cumene; chlorinated solvents such as methylene chloride, chloroform, and trichloroethylene; aprotic polar solvents such as dimethyl sulfoxide, γ-butyrolactone, and hexamethylphosphoric triamide; nitriles such as acetonitrile and propionitrile; and esters such as methyl acetate, ethyl acetate, n-propyl acetate, and n-butyl acetate.

The solvent may be used alone or in combination thereof, if necessary. The solvent may be commercially available one.

The solvent preferably has a boiling point sufficiently different from that of the product. It is rather preferred not to use any solvent besides the dialkylaniline compound (2), because a solvent occupies of a part of a reaction vessel volume to reduce the amounts of the raw materials to be fed into the reaction vessel and accordingly decrease productivity, and/or water contained in the solvent may adversely affect reactivity (see, for example, Example 4 below).

An amount of the solvent used in the alkoxymethylation is preferably 0 to 2000 g, more preferably 0 to 500 g, per mol of the alkynol compound (1).

A reaction temperature in the alkoxymethylation is preferably from −10 to 80° C., more preferably from 10 to 40° C., in view of the reactivity.

A reaction time in the alkoxymethylation varies, depending on a reaction scale, and is preferably from 1 to for 40 hours in view of the productivity.

Next, the alkoxymethyl alkynyl ether compound (4) will be described hereinafter.

In the formula (4), R is as defined for the formula (3), and "a" is as defined for the formula (1).

Specific examples of the alkoxymethyl alkynyl ether compound (4) include 3-(methoxymethoxy)-1-propyne, 3-(ethoxymethoxy)-1-propyne, 3-(propoxymethoxy)-1-propyne, 3-(butoxymethoxy)-1-propyne, 3-(pentyloxymethoxy)-1-propyne, 3-(hexoxymethoxy)-1-propyne, 3-(heptyloxymethoxy)-1-propyne, 3-(octyloxymethoxy)-1-propyne, 3-(nonyl oxymethoxy)-1-propyne, 3-(decyloxymethoxy)-1-propyne, 3-(benzyloxymethoxy)-1-propyne, 4-(methoxymethoxy)-1-butyne, 4-(ethoxymethoxy)-1-butyne, 4-(propoxymethoxy)-1-butyne, 4-(butoxymethoxy)-1-butyne, 4-(pentyloxymethoxy)-1-butyne, 4-(hexoxymethoxy)-1-butyne, 4-(heptyloxymethoxy)-1-butyne, 4-(octyloxymethoxy)-1-butyne, 4-(nonyloxymethoxy)-1-butyne, 4-(decyloxymethoxy)-1-butyne, 4-(benzyloxymethoxy)-1-butyne, 5-(methoxymethoxy)-1-pentyne, 5-(ethoxymethoxy)-1-pentyne, 5-(propoxymethoxy)-1-pentyne, 5-(butoxymethoxy)-1-pentyne, 5-(pentyloxymethoxy)-1-pentyne, 5-(hexoxymethoxy)-1-pentyne, 5-(heptyloxymethoxy)-1-pentyne, 5-(octyloxymethoxy)-1-pentyne, 5-(nonyloxymethoxy)-1-pentyne, 5-(decyloxymethoxy)-1-pentyne, 5-(benzyloxymethoxy)-1-pentyne, 6-(methoxymethoxy)-1-hexyne, 6-(ethoxymethoxy)-1-hexyne, 6-(propoxymethoxy)-1-hexyne, 6-(butoxymethoxy)-1-hexyne, 6-(pentyloxymethoxy)-1-hexyne, 6-(hexoxymethoxy)-1-hexyne, 6-(heptyloxymethoxy)-1-hexyne, 6-(octyloxymethoxy)-1-hexyne, 6-(nonyloxymethoxy)-1-hexyne, 6-(decyloxymethoxy)-1-hexyne, 6-(benzyloxymethoxy)-1-hexyne, 7-(methoxymethoxy)-1-heptyne, 7-(ethoxymethoxy)-1-heptyne, 7-(propoxymethoxy)-1-heptyne, 7-(butoxymethoxy)-1-heptyne, 7-(pentyloxymethoxy)-1-heptyne, 7-(hexoxymethoxy)-1-heptyne, 7-(heptyloxymethoxy)-1-heptyne, 7-(octyloxymethoxy)-1-heptyne, 7-(nonyloxymethoxy)-1-heptyne, 7-(decyloxymethoxy)-1-heptyne, 7-(benzyloxymethoxy)-1-heptyne, 8-(methoxymethoxy)-1-octyne, 8-(ethoxymethoxy)-1-octyne, 8-(propoxymethoxy)-1-octyne, 8-(butoxymethoxy)-1-octyne, 8-(pentyloxymethoxy)-1-octyne, 8-(hexoxymethoxy)-1-octyne, 8-(heptyloxymethoxy)-1-octyne, 8-(octyloxymethoxy)-1-octyne, 8-(nonyloxymethoxy)-1-octyne, 8-(decyloxymethoxy)-1-octyne, 8-(benzyloxymethoxy)-1-octyne, 9-(methoxymethoxy)-1-nonyne, 9-(ethoxymethoxy)-1-nonyne, 9-(propoxymethoxy)-1-nonyne, 9-(butoxymethoxy)-1-nonyne, 9-(pentyloxymethoxy)-1-nonyne, 9-(hexoxymethoxy)-1-nonyne, 9-(heptyloxymethoxy)-1-nonyne, 9-(octyloxymethoxy)-1-nonyne, 9-(nonyl oxymethoxy)-1-nonyne, 9-(decyloxymethoxy)-1-nonyne, 9-(benzyloxymethoxy)-1-nonyne, 10-(methoxymethoxy)-1-decyne, 10-(ethoxymethoxy)-1-decyne, 10-(propoxymethoxy)-1-decyne, 10-(butoxymethoxy)-1-decyne, 10-(pentyloxymethoxy)-1-decyne, 10-(hexoxymethoxy)-1-decyne, 10-(heptyloxymethoxy)-1-decyne, 10-(octyloxymethoxy)-1-decyne, 10-(nonyloxymethoxy)-1-decyne, 10-(decyloxymethoxy)-1-decyne, 10-(benzyloxymethoxy)-1-decyne, 11-(methoxymethoxy)-1-undecyne, 11-(ethoxymethoxy)-1-undecyne, 11-(propoxymethoxy)-1-undecyne, 11-(butoxymethoxy)-1-undecyne, 11-(pentyloxymethoxy)-1-undecyne, 11-(hexoxymethoxy)-1-undecyne, 11-(heptyloxymethoxy)-1-undecyne, 11-(octyloxymethoxy)-1-undecyne, 11-(nonyloxymethoxy)-1-undecyne, 11-(decyloxymethoxy)-1-undecyne, 11-(benzyloxymethoxy)-1-undecyne, 12-(methoxymethoxy)-1-dodecyne, 12-(ethoxymethoxy)-1-dodecyne, 12-(propoxymethoxy)-1-dodecyne, 12-(butoxymethoxy)-1-dodecyne, 12-(pentyloxymethoxy)-1-dodecyne, 12-(hexoxymethoxy)-1-dodecyne, 12-(heptyloxymethoxy)-1-dodecyne, 12-(octyloxymethoxy)-1-dodecyne, 12-(nonyloxymethoxy)-1-dodecyne, 12-(decyloxymethoxy)-1-dodecyne, and 12-(benzyloxymethoxy)-1-dodecyne.

Next, a step of recovering the dialkylaniline compound (2) after the completion of the alkoxymethylation and a step of reusing the recovered dialkylaniline compound (2) in a subsequent alkoxymethylation will be described hereinafter.

A step of recovering the dialkylaniline compound (2) after the completion of the alkoxymethylation will be described first.

The step of recovering the dialkylaniline compound (2) may be performed after each of the alkoxymethylations (i.e., in each batch).

In the alkoxymethylation, a hydrogen halide salt of the dialkylaniline compound (2) is by-produced together with the formation of the alkoxymethyl alkynyl ether compound (4).

Recovery of the dialkylaniline compound (2) after the alkoxymethylation include may be carried out by a method where the alkoxymethyl alkynyl ether compound (4) and the hydrogen halide salt of the dialkylaniline compound are partitioned in an acidic condition into the organic phase and the aqueous phase, respectively, after the completion of the alkoxymethylation, and the dialkylaniline compound (2) is recovered (back extraction method); a method where the alkoxymethyl alkynyl ether compound (4) and the dialkylaniline compound are separated by silica gel column chromatography, and the dialkylaniline compound (2) is recovered; and a method where the alkoxymethyl alkynyl ether compound (4) and the dialkylaniline compound are separated by distillation, and the dialkylaniline compound (2) is recovered. The third method by distillation is preferred in view of the yield and easy separation of the dialkylaniline compound (2) and the alkoxymethyl alkynyl ether compound (4).

In the recovering method by distillation, post-treatment is preferably performed before the distillation in view of the yield, as shown in the chemical reaction formula below.

Specifically, in the post-treatment, the reaction mixture (organic phase) containing the alkoxymethyl alkynyl ether compound (4) obtained in the alkoxymethylation and the hydrogen halide salt of the dialkylaniline compound is neutralized with a base in the presence of water to obtain an organic phase containing the alkoxymethyl alkynyl ether compound (4) and dialkylaniline compound (2) (neutralization step). Next, the organic phase containing the alkoxymethyl alkynyl ether compound (4) and dialkylaniline compound (2) is separated by distillation to give the alkoxymethyl alkynyl ether compound (4) and dialkylaniline compound (2) separately (distillation step).

When the base is in a solid form, it may be used as such or may be dissolved in the dialkylaniline compound (2) used in the alkoxymethylation, the aforesaid usual solvent, or water.

An amount of water used in the neutralization step is preferably from 0 to 5000 g, more preferably from 0 to 1000 g, per mol of the alkynol compound (1) having a terminal triple bond used in the alkoxymethylation, in view of the solubility and the yield.

A reaction temperature in the neutralization step is preferably from −20 to 70° C., more preferably from 0 to 40° C., in view of the reactivity.

A reaction time in the neutralization step varies, depending on a reaction scale and heat removal ability, and is preferably from 0.1 to 30 hours in view of the productivity.

A pH of the aqueous phase in the neutralization step is preferably from 4.0 to 10.0, more preferably from 5.0 to 8.0,

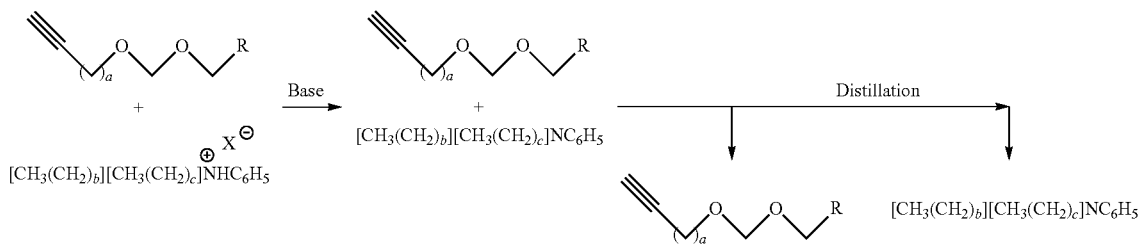

In the neutralization step, the hydrogen halide salt of the dialkylaniline compound (2) is neutralized with base to obtain the dialkylaniline compound (2) which is then partitioned into the organic phase, resulting in a mixture of the dialkylaniline compound (2) and the alkoxymethyl alkynyl ether compound (4). The dialkylaniline compound (2) serves also as an extraction solvent, so that even without any additional solvent, the alkoxymethyl alkynyl ether compound (4), which has a low molecular weight and is highly water-soluble, is extracted into the organic phase in a high yield without the compound (4) staying in the aqueous phase.

The organic phase is purified by distillation to separately recover the alkoxymethyl alkynyl ether compound (4) and dialkylaniline compound (2) in high purities.

Examples of the base used in the neutralization step include alkali metal hydroxides such as lithium hydroxide, sodium hydroxide, and potassium hydroxide; alkaline earth metal hydroxides such as calcium hydroxide, magnesium hydroxide, and barium hydroxide; alkali metal carbonates such as sodium carbonate and potassium carbonate; alkaline earth metal carbonates such as calcium carbonate, magnesium carbonate, and barium carbonate; alkali metal bicarbonates such as sodium bicarbonate and potassium bicarbonate; and alkaline earth metal bicarbonates such as calcium bicarbonate and magnesium bicarbonate. Alkali metal hydroxides such as sodium hydroxide are preferred in view of the handling.

An amount of the base used is preferably from 0.2 to 10.0 mol, more preferably 0.7 to 2.8 mol, per mol of the alkynol compound (1) used in the alkoxymethylation, in view of the recovery yield and extraction efficiency.

The base may be used either alone or in combination thereof, if necessary. The base may be commercially available one.

in view of the recovery yield of the dialkylaniline compound (2) and the extraction efficiency of the alkoxymethyl alkynyl ether compound (4).

The pH may be determined, for example, by pH test paper or by a pH meter on a sample being at a liquid temperature of 25° C.

In the neutralization step, a solvent may be used. Example of the solvent include ethers such as diethyl ether, dibutyl ether, tetrahydrofuran (THF), 4-methyltetrahydropyran, cyclopentylmethyl ether, and 1,4-dioxane; hydrocarbons such as hexane, heptane, benzene, toluene, xylene, and cumene; chlorinated solvents such as methylene chloride, chloroform, and trichloroethylene; nitriles such as acetonitrile and propionitrile; and esters such as methyl acetate, ethyl acetate, n-propyl acetate, and n-butyl acetate. It is preferred to carry out the neutralization step without adding any additional solvent, because an added solvent should be eventually removed, production efficiency would be reduced, and/or the removed additional solvent would be a waste.

Next, in the distillation step, the organic phase containing the alkoxymethyl alkynyl ether compound (4) and dialkylaniline compound (2) is separated by distillation to give these compounds separately.

The dialkylaniline compound (2) thus recovered is highly pure and can be reused in a subsequent alkoxymethylation to repeat the alkoxymethylation economically. Accordingly, the process according to the present invention is environmentally less problematic and extremely economical.

The dialkylaniline compound (2) may be recovered from one batch of the alkoxymethylation and then the recovered dialkylaniline compound (2) may be recycled to a subsequent alkoxymethylation. Alternatively, a plurality of batches of the alkoxymethylation may be carried out; the dialkylaniline compound (2) may be recovered from each one batch; the recovered dialkylaniline compound (2) may be collected; and then the collected dialkylaniline compound (2) may be recycled to a subsequent alkoxymethylation.

Thus, there is provided a process for preparing the alkoxymethyl alkynyl ether compound (4), using the dialkylaniline compound (2) as a base and extraction solvent.

EXAMPLES

The present invention will be further described with reference to the following Examples. It should be understood that the present invention is not limited to or by the Examples.

The term "purity" as used herein means an area percentage in gas chromatography (GC), unless otherwise specified. The term "production ratio" means a ratio of area percentages in GC. The yield is calculated from the area percentages in GC.

The term "yield" is calculated from the area percentages determined by GC.

In the Examples, monitoring of the reactions was carried out in the following GC conditions.

GC conditions: GC: Capillary gas chromatograph GC-2014 (Shimadzu Corporation); column: DB-5, 0.25 mm×0.25 mmϕ×30 m; carrier gas: He (1.55 mL/min), detector: FID; column temperature: 70° C., elevated in a rate of 5° C./min, and up to 230° C.

The yield was calculated according to the following equation in consideration of purities (% GC) of a starting material and a product.

Yield (%)={[(weight of a product obtained by a reaction×% GC)/molecular weight of a product]÷ [(weight of a starting material in a reaction×% GC)/molecular weight of a starting material]}×100

Example 1: Preparation of 3-(methoxymethoxy)-1-propyne (4: R=H; a=1), H—C≡CCH$_2$OCH$_2$OCH$_3$

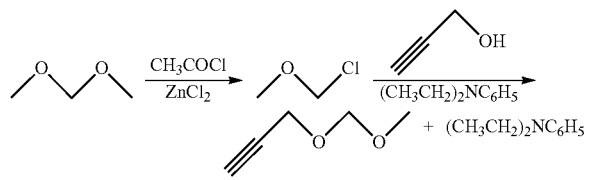

Zinc chloride (6.83 g, 0.0501 mol) and dimethoxymethane (493.05 g, 6.48 mol) were placed in a reactor at room temperature and stirred at 15 to 25° C. for 4 minutes. After the stirring, acetyl chloride (450.00 g, 5.73 mol) was added dropwise at 20 to 35° C. and stirred at 35 to 40° C. for 2 hours to prepare chloromethyl methyl ether (3: X=Cl; R=H).

Subsequently, a mixture of 2-propyn-1-ol (1: a=1) (279.01 g, 4.977 mol, purity 100%) and N,N-diethylaniline (2: b=1; c=1) (855.45 g, 5.72 mol, purity 99.82%) was added dropwise at 20 to 30° C. to the reactor containing the prepared chloromethyl methyl ether (3: X=Cl; R=H), and stirred at 20 to 30° C. for 11.5 hours. Next, an aqueous 25% by mass solution (862.88 g) of sodium hydroxide (5.39 mol) and then water (548.00 g) were added to the reaction mixture, followed by phase separation. The aqueous phase was removed to obtain the organic phase. The resulting organic phase was subjected to distillation at a reduced pressure to obtain 3-(methoxymethoxy)-1-propyne (4: R=H; a=1) (487.57 g, 4.86 mol, purity 99.89%, b.p.=76.9° C./197.8 mmHg, or 26.37 kPa) in a yield of 97.7%, and then N,N-diethylaniline (2: b=1; c=1) (825.86 g, 5.52 mol, purity 99.70%, b.p.=110.4 to 116.1° C./20.0 mmHg or 2.67 kPa) in a yield of 96.5%.

3-(Methoxymethoxy)-1-propyne (4: R=H; a=1)

Nuclear magnetic resonance spectrum: $^1$H-NMR (500 MHz, CDCl$_3$): δ=2.41 (1H, t, J=2.7 Hz, 3.36 (3H, s), 4.20 (2H, d, J=2.7 Hz), 4.69 (2H, s); $^{13}$C-NMR (500 MHz, CDCl$_3$): δ=53.95, 55.51, 74.20, 79.25, 94.69.

Mass spectrum: EI-mass spectrum (70 eV): m/z 99 (M$^r$-1), 69, 61, 55, 45, 39.

Infrared absorption spectrum (NaCl): ν=3292, 2953, 2893, 1448, 1152, 1102, 1049, 995, 938, 920, 894, 672.

N,N-Diethylaniline (2)

Nuclear magnetic resonance spectrum: $^1$H-NMR (500 MHz, CDCl$_3$): δ=1.20 (6H, t, J=6.9 Hz), 3.39 (4H, q, J=6.9 Hz), 6.68 (1H, ddt, J=7.3 Hz, 7.3 Hz, 1.1 Hz), 6.73 (2H, dd, J=9.0 Hz, 1.1 Hz), 7.25 (2H, dd, J=7.3 Hz, 5.1 Hz); $^{13}$C-NMR (500 MHz, CDCl$_3$): δ=12.53, 44.25, 111.80, 115.30, 129.21, 147.76.

Mass spectrum: EI-mass spectrum (70 eV): m/z 149 (M$^r$), 134, 120, 106, 91, 77.

Infrared absorption spectrum (NaCl): ν=2970, 2929, 2870, 1598, 1506, 1396, 1374, 1354, 1266, 1199, 1156, 1094, 1077, 1036, 1011, 791, 745, 692.

Example 2: Preparation of 4-(methoxymethoxy)-1-butyne (4: R=H; a=2), H—C≡C(CH$_2$)$_2$OCH$_2$OCH$_3$

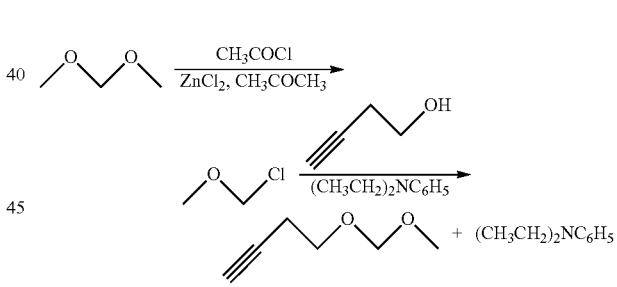

Zinc chloride (6.83 g, 0.0501 mol), dimethoxymethane (493.05 g, 6.48 mol), and methyl acetate (556.05 g) were placed in a reactor at room temperature and stirred at 15 to 25° C. for 12 minutes. After the stirring, acetyl chloride (450.00 g, 5.73 mol) was added dropwise at 20 to 35° C. and stirred at 35 to 40° C. for 2 hours to prepare chloromethyl methyl ether (3: X=Cl, R=H).

Subsequently, a mixture of 3-butyn-1-ol (1: a=2) (349.35 g, 4.98 mol, purity 99.86%) and N,N-diethylaniline (2: b=1; c=1) (855.45 g, 5.72 mol, purity 99.82%) was added dropwise at 20 to 30° C. to the reactor containing the prepared chloromethyl methyl ether (3: X=Cl; R=H), and stirred at 20 to 30° C. for 7 hours. Next, an aqueous 25% by mass solution (862.88 g) of sodium hydroxide (5.39 mol) and then water (548.00 g) and then water (568.17 g) were added to the reaction mixture, followed by phase separation. The aqueous phase was removed to obtain the organic phase. The resulting organic phase was subjected to distillation at a reduced pressure to obtain 4-(methoxymethoxy)-1-butyne (4: R=H; a=2) (564.88 g, 4.93 mol, purity 99.53%, b.p.=94.2° C./115.2 mmHg, or 15.36 kPa) in a yield of 98.9%, and then N,N-diethylaniline (2: b=1; c=1) (824.98 g, 5.51 mol, purity 99.64%, b.p.=110.4 to 116.1° C./20.0 mmHg, or 2.67 kPa) in a yield of 96.3%.

4-(methoxymethoxy)-1-butyne (4: R=H; a=2)

Nuclear magnetic resonance spectrum: $^1$H-NMR (500 MHz, CDCl$_3$): δ=1.98 (1H, t, J=2.7 Hz), 2.47 (2H, dt, J=2.6 Hz, 6.7 Hz), 3.36 (3H, s), 3.64 (2H, 6.8 Hz), 4.63 (2H, s); $^{13}$C-NMR (500 MHz, CDCl$_3$): δ=19.92, 55.20, 65.68, 69.25, 81.25, 96.33.

Mass spectrum: EI-mass spectrum (70 eV): m/z 113 (M$^+$-1), 83, 75, 61, 53, 45.

Infrared absorption spectrum (NaCl): ν=3293, 2934, 2887, 1383, 1151, 1112, 1075, 1032, 918, 646.

Example 3: Preparation of 4-(methoxymethoxy)-1-butyne (4: R=H; a=2), H—C≡C(CH$_2$)$_2$OCH$_2$OCH$_3$ Zinc chloride (6.57 g, 0.0483 mol), dimethoxymethane (474.95 g, 6.24 mol), and methyl acetate (535.64 g) were placed in a reactor at room temperature and stirred at 15 to 25° C. for 30 minutes. After the stirring, acetyl chloride (433.48 g, 5.51 mol) was added dropwise at 20 to 35° C. and stirred at 35 to 40° C. for 2 hours to prepare chloromethyl methyl ether (3: X=Cl, R=H).

Subsequently, a mixture of 3-butyn-1-ol (1: a=2) (336.52 g, 4.80 mol, purity 99.86%) and N,N-diethylaniline (2: b=1; c=1) recovered by distillation in Example 2 (824.98 g, 5.51 mol, purity 99.64%) was added dropwise at 20 to 30° C. to the reactor containing the prepared chloromethyl methyl ether (3: X=Cl; R=H), and stirred at 20 to 30° C. for 7 hours. Next, an aqueous 25% by mass solution (831.20 g) of sodium hydroxide (5.19 mol) and then water (547.31 g) were added to the reaction mixture, followed by phase separation. The aqueous phase was removed to obtain the organic phase. The resulting organic phase was subjected to distillation at a reduced pressure to obtain 4-(methoxymethoxy)-1-butyne (4: R=H; a=2) (534.66 g, 4.67 mol, purity 99.79%, b.p.=94.2° C./115.2 mmHg, or 15.36 kPa) in a yield of 97.5%, and then N,N-diethylaniline (2: b=1; c=1) (799.19 g, 5.35 mol, purity 99.80%, b.p.=110.4 to 116.1° C./20.0 mmHg, or 2.67 kPa) in a yield of 97.0%.

Various spectrum data of 4-(methoxymethoxy)-1-butyne (4) thus prepared were the same as those obtained in Example 2.

Example 4: Preparation of 4-(methoxymethoxy)-1-butyne (4: R=H; a=2), H—C≡C(CH$_2$)$_2$OCH$_2$OCH$_3$

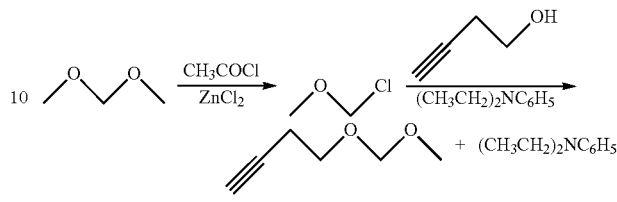

Zinc chloride (6.83 g, 0.0501 mol) and dimethoxymethane (493.05 g, 6.48 mol) were placed in a reactor at room temperature and stirred at 15 to 25° C. for 11 minutes. After the stirring, acetyl chloride (450.00 g, 5.73 mol) was added dropwise at 20 to 35° C. and stirred at 35 to 40° C. for 2 hours to prepare chloromethyl methyl ether (3: X=Cl, R=H).

Subsequently, a mixture of 3-butyn-1-ol (1: a=2) (349.35 g, 4.98 mol, purity 99.86%) and N,N-diethylaniline (2: b=1; c=1) (855.45 g, 5.72 mol, purity 99.82%) was added dropwise at 20 to 30° C. to the reactor containing the prepared chloromethyl methyl ether (3: X=Cl; R=H), and stirred at 20 to 30° C. for 5 hours. Next, an aqueous 25% by mass solution (862.88 g) of sodium hydroxide (5.39 mol) and then water (548.00 g) were added to the reaction mixture, followed by phase separation. The aqueous phase was removed to obtain the organic phase. The resulting organic phase was subjected to distillation at a reduced pressure to obtain 4-(methoxymethoxy)-1-butyne (4: R=H; a=2) (565.22 g, 4.93 mol, purity 99.50%, b.p.=94.2° C./115.2 mmHg, or 15.36 kPa) in a yield of 99.0%, and then N,N-diethylaniline (2: b=1; c=1) (847.88 g, 5.63 mol, purity 99.10%, b.p.=110.4 to 116.1° C./20.0 mmHg, or 2.67 kPa) in a yield of 98.4%.

Various spectrum data of 4-(methoxymethoxy)-1-butyne (4) thus prepared were the same as those obtained in Example 2.

Example 5: Preparation of 4-(methoxymethoxy)-1-butyne (4: R=H; a=2), H—C≡C(CH$_2$)$_2$OCH$_2$OCH$_3$

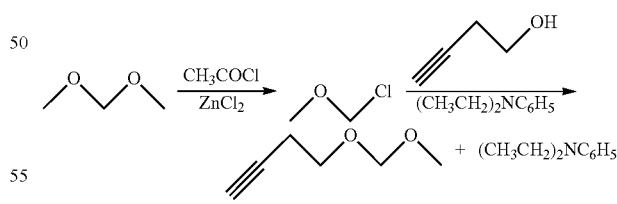

Zinc chloride (6.72 g, 0.0493 mol) and dimethoxymethane (485.34 g, 6.38 mol) were placed in a reactor at room temperature and stirred at 15 to 25° C. for 20 minutes. After the stirring, acetyl chloride (442.96 g, 5.64 mol) was added dropwise at 20 to 35° C. and stirred at 35 to 40° C. for 2 hours to prepare chloromethyl methyl ether (3: X=Cl, R=H).

Subsequently, a mixture of 3-butyn-1-ol (1: a=2) (343.89 g, 4.90 mol, purity 99.86%) and N,N-diethylaniline (2: b=1; c=1) (recovered by distillation in Example 4 847.88 g, 5.63 mol, purity 99.10%) was added dropwise at 20 to 30° C. to the reactor containing the prepared chloromethyl methyl ether (3: X=Cl; R=H), and stirred at 20 to 30° C. for 7 hours. Next, an aqueous 25% by mass solution (849.39 g) of sodium hydroxide (5.31 mol) and then water (548.00 g) and then water (559.28 g) were added to the reaction mixture, followed by phase separation. The aqueous phase was removed to obtain the organic phase. The resulting organic phase was subjected to distillation at a reduced pressure to obtain 4-(methoxymethoxy)-1-butyne (4: R=H; a=2) (549.56 g, 4.80 mol, purity 99.82%, b.p.=94.2° C./115.2 mmHg, or 15.36 kPa) in a yield of 98.1% and then N,N-diethylaniline (2: b=1; c=1) (821.67 g, 5.48 mol, purity 99.50%, b.p.=110.4 to 116.1° C./20.0 mmHg, or 2.67 kPa) in a yield of 97.3%.

Various spectrum data of 4-(methoxymethoxy)-1-butyne (4) thus prepared were the same as those obtained in Example 2.

Example 6: Preparation of 10-(methoxymethoxy)-1-decyne (4: R=H; a=8), H—C≡C(CH$_2$)$_8$OCH$_2$OCH$_3$

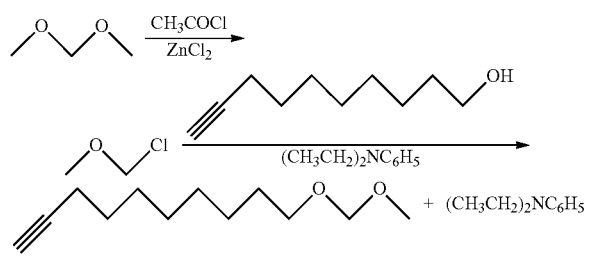

Zinc chloride (2.57 g, 0.0189 mol) and dimethoxymethane (186.16 g, 2.45 mol) were placed in a reactor at room temperature and stirred at 15 to 25° C. for 5 minutes. After the stirring, acetyl chloride (169.90 g, 2.16 mol) was added dropwise at 20 to 35° C. and stirred at 35 to 40° C. for 2 hours to prepare chloromethyl methyl ether (3: X=Cl, R=H).

Subsequently, a mixture of 9-decyn-1-ol (1: a=8) (300.98 g, 1.88 mol, purity 96.46%) and N,N-diethylaniline (2: b=1; c=1) (323.48 g, 2.16 mol, purity 99.82%) was added dropwise at 20 to 30° C. to the reactor containing the prepared chloromethyl methyl ether (3: X=Cl; R=H), and stirred at 20 to 30° C. for 7 hours. Next, an aqueous 25% by mass solution (328.98 g) of sodium hydroxide (2.06 mol) and then water (548.00 g) and then water (207.22 g) were added to the reaction mixture, followed by phase separation. The aqueous phase was removed to obtain the organic phase. The resulting organic phase was subjected to distillation at a reduced pressure to obtain N,N-diethylaniline (2: b=1; c=1) (321.31 g, 2.15 mol, purity 96.59%, b.p.=110.4 to 116.1° C./20.0 mmHg, or 2.67 kPa) in a yield of 99.7%, and then 10-(methoxymethoxy)-1-decyne (4: R=H; a=8) (377.06 g, 1.84 mol, purity 96.80%, b.p.=110.2 to 118.2° C./3.0 mmHg, or 0.40 kPa) in a yield of 97.8%.

10-(methoxymethoxy)-1-decyne (4: R=H; a=8)

Nuclear magnetic resonance spectrum: $^1$H-NMR (500 MHz, CDCl$_3$): δ=1.25-1.43 (8H, m), 1.51 (2H, q-like, J=7.3 Hz), 1.57 (2H, q-like, J=6.8 Hz), 1.92 (1H, t, J=2.7 Hz), 2.16 (2H, td, J=7.3 Hz, 2.7 Hz), 3.34 (3H, s), 3.50 (2H, t, J=6.9 Hz), 4.60 (2H, s); $^{13}$C-NMR (500 MHz, CDCl$_3$): δ=18.33, 26.11, 28.40, 28.63, 28.99, 29.23, 29.67, 55.02, 67.77, 68.04, 84.67, 96.33.

Mass spectrum: EI-mass spectrum (70 eV): m/z 197 (M$^+$-1), 183, 165, 135, 121, 107, 95, 81, 67, 45.

Infrared absorption spectrum (NaCl): ν=3308, 2932, 2857, 1465, 1145, 1111, 1051, 919, 630.

Example 7: Preparation of 3-(ethoxymethoxy)-1-propyne (4: R=CH$_3$; a=1), H—C≡CCH$_2$OCH$_2$OCH$_2$CH$_3$

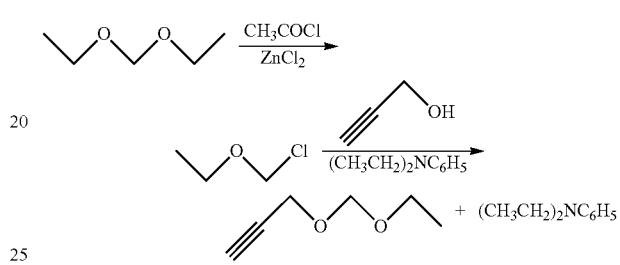

Zinc chloride (6.83 g, 0.0501 mol) and diethoxymethane (673.86 g, 6.47 mol) were placed in a reactor at room temperature and stirred at 15 to 25° C. for 13 minutes. After the stirring, acetyl chloride (450.00 g, 5.73 mol) was added dropwise at 20 to 35° C. and stirred at 35 to 40° C. for 2 hours to prepare chloromethyl ethyl ether (3: X=Cl, R=CH$_3$).

Subsequently, a mixture of 2-propyn-1-ol (1: a=1) (279.01 g, 4.977 mol, purity 100%) and N,N-diethylaniline (2: b=1; c=1) (855.45 g, 5.72 mol, purity 99.82%) was added dropwise at 20 to 30° C. to the reactor containing the prepared chloromethyl ethyl ether (3: X=Cl; R=CH$_3$), and stirred at 20 to 30° C. for 5.5 hours. Next, an aqueous 25% by mass solution (862.88 g) of sodium hydroxide (5.39 mol) and then water (548.00 g) were added to the reaction mixture, followed by phase separation. The aqueous phase was removed to obtain the organic phase. The resulting organic phase was subjected to distillation at a reduced pressure to obtain 3-(ethoxymethoxy)-1-propyne (4: R=CH$_3$; a=1) (552.28 g, 4.82 mol, purity 99.64%, b.p.=94.8° C./235.4 mmHg, or 31.38 kPa) in a yield of 96.9%, and then N,N-diethylaniline (2: b=1; c=1) (808.40 g, 5.41 mol, purity 99.91%, b.p.=110.4 to 116.1° C./20.0 mmHg, or 2.67 kPa) in a yield of 94.6%.

3-(Ethoxymethoxy)-1-propyne (4: R=CH$_3$; a=1)

Nuclear magnetic resonance spectrum: $^1$H-NMR (500 MHz, CDCl$_3$): δ=1.20 (3H, t, J=7.3 Hz), 2.40 (1H, t, J=2.7 Hz), 3.60 (2H, q, J=7.3 Hz), 4.21 (2H, d, J=2.7 Hz), 4.74 (2H, s); $^{13}$C-NMR (500 MHz, CDCl$_3$): δ=15.02, 53.97, 63.60, 74.11, 79.37, 93.36.

Mass spectrum: EI-mass spectrum (70 eV): m/z 113 (M$^+$-1), 85, 69, 55, 39.

Infrared absorption spectrum (NaCl): ν=3294, 2978, 2935, 2887, 1393, 1180, 1151, 1111, 1049, 1018, 996, 938, 895, 667.

Comparative Example 1: Preparation of
3-(methoxymethoxy)-1-propyne (4: R=H; a=1),
H—C≡CCH$_2$OCH$_2$OCH$_3$

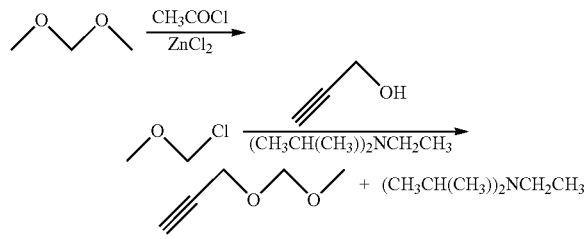

Zinc chloride (6.83 g, 0.0501 mol) and dimethoxymethane (493.05 g, 6.48 mol) were placed in a reactor at room temperature and stirred at 15 to 25° C. for 5 minutes. After the stirring, acetyl chloride (450.00 g, 5.73 mol) was added dropwise at 20 to 35° C. and stirred at 35 to 40° C. for 2 hours to prepare chloromethyl methyl ether (3: X=Cl, R=H).

Subsequently, a mixture of 2-propyn-1-ol (1: a=1) (279.01 g, 4.977 mol, purity 100%) and N,N-diisopropylethylamine (739.58 g, 5.72 mol, purity 100%) was added dropwise at 20 to 30° C. to the reactor containing the prepared chloromethyl methyl ether (3: X=Cl; R=H), and stirred at 20 to 30° C. for 8.0 hours. Next, an aqueous 25% by mass solution (862.88 g) of sodium hydroxide (5.39 mol) and then water (548.00 g) were added to the reaction mixture, followed by phase separation. The aqueous phase was removed to obtain the organic phase. The resulting organic phase was subjected to distillation at a reduced pressure to obtain 1047.08 g of a mixture of 3-(methoxymethoxy)-1-propyne (4: R=H; a=1) (3.50 mol, yield 70.4%) and N,N-diisopropylethylamine (5.39 mol, yield 94.3%), wherein the boiling point of the mixture ranges from 85.1° C./408.3 mmHg, or 54.44 kPa to 101.5° C./378.2 mmHg, or 50.42 kPa.

A GC % ratio of 3-(methoxymethoxy)-1-propyne (4: R=H; a=1) to N,N-diisopropylethylamine increased from a first half of the distillation progress to a latter half of the distillation progress. Accordingly, it is surmised that N,N-diisopropylethylamine has a slightly higher boiling point than 3-(methoxymethoxy)-1-propyne (4: R=H; a=1), but they could not be separated by distillation.

The invention claimed is:

1. A process for preparing an alkoxymethyl alkynyl ether compound having a terminal triple bond of the following formula (4):

H—C≡C(CH$_2$)$_a$OCH$_2$OCH$_2$R  (4)

wherein R represents a hydrogen atom, an n-alkyl group having 1 to 9 carbon atoms, or a phenyl group, and "a" represents an integer of 1 to 10, the method comprising:
subjecting an alkynol compound having a terminal triple bond of the following formula (1):

H—C≡C(CH$_2$)$_a$OH  (1)

wherein a is as defined above,
to an alkoxymethylation with a halomethyl alkyl ether compound of the following formula (3):

RCH$_2$OCH$_2$X  (3)

wherein X represents a halogen atom, and R is as defined above, in the presence of a dialkylaniline compound of the following formula (2) as a base:

[CH$_3$(CH$_2$)$_b$][CH$_3$(CH$_2$)$_c$]NC$_6$H$_5$  (2)

wherein b and c represent, independently of each other, an integer of 0 to 9,
to form the alkoxymethyl alkynyl ether compound (4) having a terminal triple bond,
wherein:
(i) the alkoxymethylation is carried out without any additional solvent other than the dialkylaniline compound (2), or
(ii) the method further comprises a post-treatment that is carried out by subjecting a reaction mixture comprising the alkoxymethyl alkynyl ether compound (4) to a neutralization with a base other than the dialkylaniline compound (2) in the presence of water, or
(iii) the alkoxymethylation is carried out without any additional solvent other than the dialkylaniline compound (2), and the method further comprises a post-treatment that is carried out by subjecting a reaction mixture comprising the alkoxymethyl alkynyl ether compound (4) to a neutralization with a base other than the dialkylaniline compound (2) in the presence of water.

2. The process for preparing an alkoxymethyl alkynyl ether compound (4) having a terminal triple bond according to claim 1, wherein the alkynol compound (1) and the dialkylaniline compound (2) are added dropwise to the halomethyl alkyl ether compound (3) to proceed with the alkoxymethylation.

3. The process for preparing an alkoxymethyl alkynyl ether compound (4) having a terminal triple bond according to claim 1, the method further comprising reacting a dialkoxymethane compound of the following formula (5):

RCH$_2$OCH$_2$OCH$_2$R  (5)

wherein R is as defined above,
with a halogenating agent (7) in the presence of a zinc compound (6) to form the halomethyl alkyl ether compound (3).

4. The process for preparing an alkoxymethyl alkynyl ether compound (4) having a terminal triple bond according to claim 1, wherein the halomethyl alkyl ether compound (3) is selected from the group consisting of chloromethyl methyl ether, chloromethyl ethyl ether, chloromethyl propyl ether, chloromethyl butyl ether, and chloromethyl benzyl ether.

5. The process for preparing an alkoxymethyl alkynyl ether compound (4) having a terminal triple bond according to claim 1, wherein the dialkylaniline compound (2) is selected from the group consisting of N,N-dimethylaniline, N,N-diethylaniline, N,N-dipropylaniline, and N,N-dibutylaniline.

6. The process for preparing an alkoxymethyl alkynyl ether compound (4) having a terminal triple bond according to claim 1, wherein the alkynol compound (1) is selected from the group consisting of 2-propyn-1-ol, 3-butyn-1-ol, 4-pentyn-1-ol, and 5-hexyn-1-ol.

7. The process for preparing an alkoxymethyl alkynyl ether compound (4) having a terminal triple bond according to claim 1, the method further comprising recovering the dialkylaniline compound (2) after the alkoxymethylation.

8. The process for preparing an alkoxymethyl alkynyl ether compound (4) having a terminal triple bond according to claim 7, the method further comprising recycling the recovered dialkylaniline compound (2) to a subsequent alkoxymethylation.

9. The process for preparing an alkoxymethyl alkynyl ether compound (4) having a terminal triple bond according to claim 7, wherein the dialkylaniline compound (2) is recovered from one batch of the alkoxymethylation and then the recovered dialkylaniline compound (2) is recycled to a subsequent alkoxymethylation; or a plurality of batches of the alkoxymethylation is carried out, and the dialkylaniline compound (2) is recovered from each one batch, and the recovered dialkylaniline compound (2) is collected, and then the collected dialkylaniline compound (2) is recycled to a subsequent alkoxymethylation.

10. The process for preparing an alkoxymethyl alkynyl ether compound (4) having a terminal triple bond according to claim 8, wherein the dialkylaniline compound (2) is recovered from one batch of the alkoxymethylation and then the recovered dialkylaniline compound (2) is recycled to a subsequent alkoxymethylation; or a plurality of batches of the alkoxymethylation is carried out, and the dialkylaniline compound (2) is recovered from each one batch, and the recovered dialkylaniline compound (2) is collected, and then the collected dialkylaniline compound (2) is recycled to a subsequent alkoxymethylation.

11. The process for preparing an alkoxymethyl alkynyl ether compound (4) having a terminal triple bond according to claim 2, the method further comprising reacting a dialkoxymethane compound of the following formula (5):

$$RCH_2OCH_2OCH_2R \quad (5)$$

wherein R is as defined above,
with a halogenating agent (7) in the presence of a zinc compound (6) to form the halomethyl alkyl ether compound (3).

12. The process for preparing an alkoxymethyl alkynyl ether compound (4) having a terminal triple bond according to claim 2, wherein the halomethyl alkyl ether compound (3) is selected from the group consisting of chloromethyl methyl ether, chloromethyl ethyl ether, chloromethyl propyl ether, chloromethyl butyl ether, and chloromethyl benzyl ether.

13. The process for preparing an alkoxymethyl alkynyl ether compound (4) having a terminal triple bond according to claim 2, wherein the dialkylaniline compound (2) is selected from the group consisting of N,N-dimethylaniline, N,N-diethylaniline, N,N-dipropylaniline, and N,N-dibutylaniline.

14. The process for preparing an alkoxymethyl alkynyl ether compound (4) having a terminal triple bond according to claim 2, wherein the alkynol compound (1) is selected from the group consisting of 2-propyn-1-ol, 3-butyn-1-ol, 4-pentyn-1-ol, and 5-hexyn-1-ol.

15. The process for preparing an alkoxymethyl alkynyl ether compound (4) having a terminal triple bond according to claim 2, the method further comprising recovering the dialkylaniline compound (2) after the alkoxymethylation.

16. The process for preparing an alkoxymethyl alkynyl ether compound (4) having a terminal triple bond according to claim 3, wherein the halomethyl alkyl ether compound (3) is selected from the group consisting of chloromethyl methyl ether, chloromethyl ethyl ether, chloromethyl propyl ether, chloromethyl butyl ether, and chloromethyl benzyl ether.

17. The process for preparing an alkoxymethyl alkynyl ether compound (4) having a terminal triple bond according to claim 3, wherein the dialkylaniline compound (2) is selected from the group consisting of N,N-dimethylaniline, N,N-diethylaniline, N,N-dipropylaniline, and N,N-dibutylaniline.

18. The process for preparing an alkoxymethyl alkynyl ether compound (4) having a terminal triple bond according to claim 3, wherein the alkynol compound (1) is selected from the group consisting of 2-propyn-1-ol, 3-butyn-1-ol, 4-pentyn-1-ol, and 5-hexyn-1-ol.

19. The process for preparing an alkoxymethyl alkynyl ether compound (4) having a terminal triple bond according to claim 3 the method further comprising recovering the dialkylaniline compound (2) after the alkoxymethylation.

20. The process for preparing an alkoxymethyl alkynyl ether compound (4) having a terminal triple bond according to claim 4, wherein the dialkylaniline compound (2) is selected from the group consisting of N,N-dimethylaniline, N,N-diethylaniline, N,N-dipropylaniline, and N,N-dibutylaniline.

21. The process for preparing an alkoxymethyl alkynyl ether compound (4) having a terminal triple bond according to claim 1, wherein the alkoxymethylation is carried out without any additional solvent other than the dialkylaniline compound (2).

22. The process for preparing an alkoxymethyl alkynyl ether compound (4) having a terminal triple bond according to claim 1, wherein the method further comprises a post-treatment that is carried out by subjecting a reaction mixture comprising the alkoxymethyl alkynyl ether compound (4) to a neutralization with a base other than the dialkylaniline compound (2) in the presence of water.

23. The process for preparing an alkoxymethyl alkynyl ether compound (4) having a terminal triple bond according to claim 1, wherein the alkoxymethylation is carried out without any additional solvent other than the dialkylaniline compound (2), and the method further comprises a post-treatment that is carried out by subjecting a reaction mixture comprising the alkoxymethyl alkynyl ether compound (4) to a neutralization with a base other than the dialkylaniline compound (2) in the presence of water.

24. The process for preparing an alkoxymethyl alkynyl ether compound (4) having a terminal triple bond according to claim 22, wherein, after the neutralization, water is added to the reaction mixture, followed by phase separation of the reaction mixture, and an aqueous phase of the reaction mixture is removed to obtain an organic phase containing the alkoxymethyl alkynyl ether compound (4) and dialkylaniline compound (2), and wherein the method further comprises distilling the organic phase to provide the alkoxymethyl alkynyl ether compound (4) and dialkylaniline compound (2) separately.

25. The process for preparing an alkoxymethyl alkynyl ether compound (4) having a terminal triple bond according to claim 23, wherein, after the neutralization, water is added to the reaction mixture, followed by phase separation of the reaction mixture, and an aqueous phase of the reaction mixture is removed to obtain an organic phase containing the alkoxymethyl alkynyl ether compound (4) and dialkylaniline compound (2), and wherein the method further comprises distilling the organic phase to provide the alkoxymethyl alkynyl ether compound (4) and dialkylaniline compound (2) separately.

26. The process for preparing an alkoxymethyl alkynyl ether compound (4) having a terminal triple bond according to claim 22, wherein the base used in the neutralization step is selected from an alkali metal hydroxide, an alkaline earth metal hydroxide, an alkali metal carbonate, an alkaline earth metal carbonate, an alkali metal bicarbonate, an alkaline earth metal bicarbonate, and any combination thereof.

27. The process for preparing an alkoxymethyl alkynyl ether compound (4) having a terminal triple bond according to claim 23, wherein the base used in the neutralization step is selected from an alkali metal hydroxide, an alkaline earth metal hydroxide, an alkali metal carbonate, an alkaline earth metal carbonate, an alkali metal bicarbonate, an alkaline earth metal bicarbonate, and any combination thereof.

* * * * *

UNITED STATES PATENT AND TRADEMARK OFFICE
CERTIFICATE OF CORRECTION

| | | |
|---|---|---|
| PATENT NO. | : 11,384,041 B2 | Page 1 of 1 |
| APPLICATION NO. | : 17/128306 | |
| DATED | : July 12, 2022 | |
| INVENTOR(S) | : Miyake et al. | |

It is certified that error appears in the above-identified patent and that said Letters Patent is hereby corrected as shown below:

In the Specification

Column 3, Line 63: Please correct "RCH$_2$OCH$_2$X" to read --R(CH$_2$)$_d$OCH$_2$X--

Column 12, Line 14-15: Please correct "(M$^t$-1)" to read --(M$^+$-1)--

Column 12, Line 27: Please correct "(M$^t$)" to read --(M$^+$)--

Signed and Sealed this
Eighteenth Day of April, 2023

Katherine Kelly Vidal
*Director of the United States Patent and Trademark Office*